(12) United States Patent
Lauffer

(10) Patent No.: US 9,060,063 B2
(45) Date of Patent: *Jun. 16, 2015

(54) METHOD AND SYSTEM TO CONNECT CONSUMERS TO INFORMATION

(71) Applicant: YP Interactive LLC, Wilmington, DE (US)

(72) Inventor: Randall B. Lauffer, Brookline, MA (US)

(73) Assignee: YELLOWPAGES.COM LLC, Tucker, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/786,201

(22) Filed: Mar. 5, 2013

(65) Prior Publication Data

US 2013/0182834 A1 Jul. 18, 2013

Related U.S. Application Data

(63) Continuation of application No. 12/768,664, filed on Apr. 27, 2010, now Pat. No. 8,396,735, which is a continuation of application No. 11/772,525, filed on Jul. 2, 2007, now Pat. No. 7,729,938, which is a (Continued)

(51) Int. Cl.
*H04M 3/51* (2006.01)
*G06Q 10/06* (2012.01)

(Continued)

(52) U.S. Cl.
CPC ......... *H04M 3/5191* (2013.01); *G06Q 10/0631* (2013.01); *G06Q 10/06311* (2013.01); *G06Q 10/063112* (2013.01); *G06Q 10/0639* (2013.01); *G06Q 10/06398* (2013.01); *G06Q 20/102* (2013.01); *G06Q 30/02* (2013.01); *G06Q 30/0206* (2013.01); *G06Q 30/0241* (2013.01);

(Continued)

(58) Field of Classification Search
CPC ..................... G06Q 10/063112; H04M 3/5191
USPC ..................................... 705/7.14; 379/265.12
See application file for complete search history.

(56) References Cited

U.S. PATENT DOCUMENTS

| | | |
|---|---|---|
| 4,313,035 A | 1/1982 | Jordan et al. |
| 4,577,065 A | 3/1986 | Frey et al. |

(Continued)

FOREIGN PATENT DOCUMENTS

| | | |
|---|---|---|
| AU | 699785 | 5/1995 |
| GB | 2329046 | 3/1999 |

(Continued)

OTHER PUBLICATIONS

Greenberg, Ken, "Jambo Launches to Connect People and Businesses from the Internet to the Phone," Market Wire, May 3, 2005.

(Continued)

*Primary Examiner* — Susanna M Meinecke Diaz
(74) *Attorney, Agent, or Firm* — Kilpatrick Townsend & Stockton LLP

(57) ABSTRACT

This invention provides for a method of (or apparatus for) facilitating the delivery of advice to consumers using a server unit which can store and display the names and characteristics of experts and then rapidly assist in connecting the expert and consumer for real-time communication. The server can also have the ability to receive keywords from the consumer, match those keywords to one or more experts, and tell the consumer how to contact an expert.

21 Claims, 2 Drawing Sheets

Diverse Advice Sources

Information Flow:

Compensation for Advice:

Related U.S. Application Data continuation of application No. 10/951,502, filed on Sep. 27, 2004, now Pat. No. 7,249,045, which is a continuation of application No. 10/107,743, filed on Mar. 26, 2002, now Pat. No. 6,801,899, which is a continuation of application No. 09/488,130, filed on Jan. 20, 2000, now Pat. No. 6,223,165.

(60) Provisional application No. 60/125,557, filed on Mar. 22, 1999.

(51) Int. Cl.
| | |
|---|---|
| *G06Q 20/10* | (2012.01) |
| *G06Q 30/02* | (2012.01) |
| *G06Q 30/06* | (2012.01) |
| *G06Q 50/24* | (2012.01) |
| *G06Q 99/00* | (2006.01) |
| *H01L 29/49* | (2006.01) |
| *H01L 29/66* | (2006.01) |
| *H01L 29/786* | (2006.01) |

(52) U.S. Cl.
CPC ............ *G06Q 30/06* (2013.01); *G06Q 30/0601* (2013.01); *G06Q 30/0613* (2013.01); *G06Q 50/24* (2013.01); *G06Q 99/00* (2013.01); *H01L 29/4908* (2013.01); *H01L 29/66757* (2013.01); *H01L 29/78675* (2013.01)

(56) References Cited

U.S. PATENT DOCUMENTS

| | | | |
|---|---|---|---|
| 4,631,428 A | 12/1986 | Grimes | |
| 4,645,873 A | 2/1987 | Chomet | |
| 4,677,434 A | 6/1987 | Fascenda | |
| 4,723,283 A | 2/1988 | Nagasawa et al. | |
| 4,751,669 A | 6/1988 | Sturgis et al. | |
| 4,752,675 A | 6/1988 | Zetmeir | |
| 4,847,890 A | 7/1989 | Solomon et al. | |
| 4,850,007 A | 7/1989 | Marino et al. | |
| 4,878,239 A | 10/1989 | Solomon et al. | |
| 4,963,995 A | 10/1990 | Lang | |
| 5,017,917 A | 5/1991 | Fisher et al. | |
| 5,057,932 A | 10/1991 | Lang | |
| 5,058,152 A | 10/1991 | Solomon et al. | |
| 5,148,474 A | 9/1992 | Haralambopoulos et al. | |
| 5,155,743 A | 10/1992 | Jacobs | |
| 5,164,839 A | 11/1992 | Lang | |
| 5,262,875 A | 11/1993 | Mincer et al. | |
| 5,319,542 A | 6/1994 | King, Jr. et al. | |
| 5,325,424 A | 6/1994 | Grube | |
| 5,347,632 A | 9/1994 | Filepp et al. | |
| 5,359,508 A | 10/1994 | Rossides | |
| 5,361,295 A | 11/1994 | Solomon et al. | |
| 5,369,694 A | 11/1994 | Bales et al. | |
| 5,440,334 A | 8/1995 | Walters et al. | |
| 5,448,625 A | 9/1995 | Lederman | |
| 5,453,352 A | 9/1995 | Tachibana | |
| 5,497,502 A | 3/1996 | Castille | |
| 5,524,146 A | 6/1996 | Morrisey et al. | |
| 5,533,103 A | 7/1996 | Peavey et al. | |
| 5,537,314 A | 7/1996 | Kanter | |
| 5,539,735 A | 7/1996 | Moskowitz | |
| 5,555,298 A | 9/1996 | Jonsson | |
| 5,557,677 A | 9/1996 | Prytz | |
| 5,574,780 A | 11/1996 | Andruska et al. | |
| 5,574,781 A | 11/1996 | Blaze | |
| 5,589,892 A | 12/1996 | Knee et al. | |
| 5,590,197 A | 12/1996 | Chen et al. | |
| 5,596,634 A | 1/1997 | Fernandez et al. | |
| 5,602,905 A | 2/1997 | Mettke | |
| 5,604,803 A | 2/1997 | Aziz | |
| 5,608,786 A | 3/1997 | Gordon | |
| 5,615,213 A | 3/1997 | Griefer | |
| 5,619,148 A | 4/1997 | Guo | |
| 5,619,570 A | 4/1997 | Tsutsui | |
| 5,619,725 A | 4/1997 | Gordon | |
| 5,619,991 A | 4/1997 | Sloane | |
| 5,623,536 A | 4/1997 | Solomon et al. | |
| 5,634,012 A | 5/1997 | Stefik et al. | |
| 5,638,432 A | 6/1997 | Wille et al. | |
| 5,651,058 A | 7/1997 | Hackett-Jones et al. | |
| 5,668,953 A | 9/1997 | Sloo | |
| 5,675,734 A | 10/1997 | Hair | |
| 5,694,163 A | 12/1997 | Harrison | |
| 5,694,549 A | 12/1997 | Carlin et al. | |
| 5,696,965 A | 12/1997 | Dedrick | |
| 5,701,419 A | 12/1997 | McConnell | |
| 5,710,887 A | 1/1998 | Chelliah et al. | |
| 5,710,970 A | 1/1998 | Walters et al. | |
| 5,712,979 A | 1/1998 | Graber et al. | |
| 5,715,314 A | 2/1998 | Payne et al. | |
| 5,717,860 A | 2/1998 | Graber et al. | |
| 5,718,247 A | 2/1998 | Frankel | |
| 5,721,763 A | 2/1998 | Joseph et al. | |
| 5,722,418 A | 3/1998 | Bro | |
| 5,724,424 A | 3/1998 | Gifford | |
| 5,724,521 A | 3/1998 | Dedrick | |
| 5,734,961 A | 3/1998 | Castille | |
| 5,740,231 A | 4/1998 | Cohn et al. | |
| 5,745,681 A | 4/1998 | Levine et al. | |
| 5,751,956 A | 5/1998 | Kirsch | |
| 5,768,348 A | 6/1998 | Solomon et al. | |
| 5,768,521 A | 6/1998 | Dedrick | |
| 5,774,534 A | 6/1998 | Mayer | |
| 5,778,367 A | 7/1998 | Wesinger, Jr. et al. | |
| 5,781,894 A | 7/1998 | Petrecca et al. | |
| 5,793,851 A | 8/1998 | Albertson | |
| 5,794,221 A | 8/1998 | Egendorf | |
| 5,802,502 A | 9/1998 | Gell et al. | |
| 5,809,119 A | 9/1998 | Tonomura et al. | |
| 5,809,145 A | 9/1998 | Slik et al. | |
| 5,812,769 A | 9/1998 | Graber et al. | |
| 5,818,836 A | 10/1998 | DuVal | |
| 5,819,092 A | 10/1998 | Ferguson et al. | |
| 5,819,267 A | 10/1998 | Uyama | |
| 5,819,271 A | 10/1998 | Mahoney et al. | |
| 5,819,285 A | 10/1998 | Damico et al. | |
| 5,825,869 A | 10/1998 | Brooks et al. | |
| 5,825,876 A | 10/1998 | Peterson, Jr. | |
| 5,832,523 A | 11/1998 | Kanai et al. | |
| 5,835,896 A | 11/1998 | Fisher et al. | |
| 5,842,212 A | 11/1998 | Ballurio et al. | |
| 5,850,433 A | 12/1998 | Rondeau | |
| 5,860,068 A | 1/1999 | Cook | |
| 5,862,223 A * | 1/1999 | Walker et al. ................... 705/50 |
| 5,864,871 A | 1/1999 | Kitain et al. | |
| RE36,111 E | 2/1999 | Neville | |
| 5,870,546 A | 2/1999 | Kirsch | |
| 5,870,744 A | 2/1999 | Sprague | |
| 5,878,130 A | 3/1999 | Andrews et al. | |
| 5,884,032 A | 3/1999 | Bateman et al. | |
| 5,884,272 A | 3/1999 | Walker et al. | |
| 5,884,282 A | 3/1999 | Robinson | |
| 5,889,774 A | 3/1999 | Mirashrafi et al. | |
| 5,890,138 A | 3/1999 | Godin et al. | |
| 5,893,077 A | 4/1999 | Griffin | |
| 5,901,214 A | 5/1999 | Shaffer et al. | |
| 5,903,635 A | 5/1999 | Kaplan | |
| 5,907,677 A | 5/1999 | Glenn et al. | |
| 5,911,132 A | 6/1999 | Sloane | |
| 5,914,951 A | 6/1999 | Bentley et al. | |
| 5,924,082 A | 7/1999 | Silverman et al. | |
| 5,937,390 A | 8/1999 | Hyodo | |
| 5,940,471 A | 8/1999 | Homayoun | |
| 5,940,484 A | 8/1999 | DeFazio et al. | |
| 5,946,646 A | 8/1999 | Schena et al. | |
| 5,960,069 A * | 9/1999 | Felger ................... 379/114.01 |
| 5,960,416 A | 9/1999 | Block | |
| 5,963,202 A | 10/1999 | Polish | |
| 5,963,861 A | 10/1999 | Hanson | |
| 5,974,141 A | 10/1999 | Saito | |
| 5,974,398 A | 10/1999 | Hanson et al. | |

(56) References Cited

U.S. PATENT DOCUMENTS

| | | |
|---|---|---|
| 5,978,567 A | 11/1999 | Rebane et al. |
| 5,982,863 A | 11/1999 | Smiley et al. |
| 5,987,102 A | 11/1999 | Elliott et al. |
| 5,987,118 A | 11/1999 | Dickerman et al. |
| 5,987,430 A | 11/1999 | Van Horne et al. |
| 5,991,394 A | 11/1999 | Dezonno et al. |
| 5,995,705 A | 11/1999 | Lang |
| 5,999,609 A | 12/1999 | Nishimura |
| 5,999,611 A | 12/1999 | Tatchell et al. |
| 5,999,965 A | 12/1999 | Kelly |
| 6,006,197 A | 12/1999 | D'Eon et al. |
| 6,011,794 A | 1/2000 | Mordowitz et al. |
| 6,014,644 A | 1/2000 | Erickson |
| 6,026,087 A | 2/2000 | Mirashrafi et al. |
| 6,026,148 A | 2/2000 | Dworkin et al. |
| 6,026,375 A | 2/2000 | Hall et al. |
| 6,026,400 A | 2/2000 | Suzuki |
| 6,028,601 A | 2/2000 | Machiraju et al. |
| 6,029,141 A | 2/2000 | Bezos et al. |
| 6,035,021 A | 3/2000 | Katz |
| 6,046,762 A | 4/2000 | Sonesh et al. |
| 6,049,779 A * | 4/2000 | Berkson .................... 705/14.39 |
| 6,055,513 A | 4/2000 | Katz et al. |
| 6,058,379 A | 5/2000 | Odom et al. |
| 6,064,978 A | 5/2000 | Gardner et al. |
| 6,108,704 A | 8/2000 | Hutton et al. |
| 6,130,933 A | 10/2000 | Miloslavsky |
| 6,144,670 A | 11/2000 | Sponaugle et al. |
| 6,167,449 A | 12/2000 | Arnold et al. |
| 6,173,279 B1 | 1/2001 | Levin et al. |
| 6,175,619 B1 | 1/2001 | DeSimone |
| 6,185,194 B1 | 2/2001 | Musk et al. |
| 6,188,673 B1 | 2/2001 | Bauer et al. |
| 6,188,761 B1 | 2/2001 | Dickerman et al. |
| 6,189,030 B1 | 2/2001 | Kirsch et al. |
| 6,192,050 B1 | 2/2001 | Stovall |
| 6,199,096 B1 | 3/2001 | Mirashrafi et al. |
| 6,208,713 B1 | 3/2001 | Rahrer et al. |
| 6,212,192 B1 | 4/2001 | Mirashrafi et al. |
| 6,216,111 B1 | 4/2001 | Walker et al. |
| 6,223,165 B1 | 4/2001 | Lauffer |
| 6,230,287 B1 * | 5/2001 | Pinard et al. .................... 714/31 |
| 6,243,684 B1 | 6/2001 | Stuart et al. |
| 6,259,774 B1 | 7/2001 | Miloslavsky |
| 6,269,336 B1 | 7/2001 | Ladd et al. |
| 6,269,361 B1 | 7/2001 | Davis et al. |
| 6,275,490 B1 | 8/2001 | Mattaway et al. |
| 6,292,799 B1 | 9/2001 | Peek et al. |
| 6,298,056 B1 | 10/2001 | Pendse |
| 6,301,342 B1 | 10/2001 | Ander et al. |
| 6,304,637 B1 | 10/2001 | Mirashrafi et al. |
| 6,310,941 B1 | 10/2001 | Crutcher et al. |
| 6,314,402 B1 | 11/2001 | Monaco et al. |
| 6,323,894 B1 | 11/2001 | Katz |
| 6,327,572 B1 | 12/2001 | Morton et al. |
| 6,385,583 B1 | 5/2002 | Ladd et al. |
| 6,393,117 B1 | 5/2002 | Trell |
| 6,400,806 B1 | 6/2002 | Uppaluru |
| 6,404,864 B1 | 6/2002 | Evslin et al. |
| 6,404,877 B1 | 6/2002 | Bolduc et al. |
| 6,404,884 B1 | 6/2002 | Marwell et al. |
| 6,408,278 B1 | 6/2002 | Carney et al. |
| 6,430,276 B1 | 8/2002 | Bouvier et al. |
| 6,434,527 B1 | 8/2002 | Horvitz |
| 6,445,694 B1 | 9/2002 | Swartz |
| 6,463,136 B1 | 10/2002 | Malik |
| 6,466,966 B1 | 10/2002 | Kirsch et al. |
| 6,470,079 B1 | 10/2002 | Benson |
| 6,470,181 B1 | 10/2002 | Maxwell |
| 6,470,317 B1 | 10/2002 | Ladd et al. |
| 6,482,156 B2 | 11/2002 | Iliff |
| 6,484,148 B1 | 11/2002 | Boyd |
| 6,493,437 B1 | 12/2002 | Olshansky |
| 6,493,671 B1 | 12/2002 | Ladd et al. |
| 6,493,673 B1 | 12/2002 | Ladd et al. |
| 6,510,417 B1 | 1/2003 | Woods et al. |
| 6,516,057 B2 | 2/2003 | Meek et al. |
| 6,523,010 B2 | 2/2003 | Lauffer |
| 6,529,878 B2 | 3/2003 | De Rafael et al. |
| 6,529,946 B2 | 3/2003 | Yokono et al. |
| 6,539,359 B1 | 3/2003 | Ladd et al. |
| 6,546,372 B2 | 4/2003 | Lauffer |
| 6,549,889 B2 | 4/2003 | Lauffer |
| 6,560,576 B1 | 5/2003 | Cohen et al. |
| 6,606,376 B1 | 8/2003 | Trell |
| 6,625,595 B1 | 9/2003 | Anderson et al. |
| 6,636,590 B1 | 10/2003 | Jacob et al. |
| 6,658,389 B1 | 12/2003 | Alpdemir |
| 6,704,403 B2 | 3/2004 | Lurie et al. |
| 6,731,736 B2 | 5/2004 | Meek et al. |
| 6,735,588 B2 | 5/2004 | Kim et al. |
| 6,757,364 B2 | 6/2004 | Newkirk |
| 6,760,537 B2 | 7/2004 | Mankovitz |
| 6,769,020 B2 | 7/2004 | Miyazaki et al. |
| 6,770,029 B2 | 8/2004 | Iliff |
| 6,801,899 B2 | 10/2004 | Lauffer |
| 6,807,532 B1 | 10/2004 | Kolls |
| 6,813,346 B2 | 11/2004 | Gruchala et al. |
| 6,826,194 B1 * | 11/2004 | Vered et al. .................... 370/449 |
| 6,836,225 B2 | 12/2004 | Lee et al. |
| 6,847,992 B1 | 1/2005 | Haitsuka et al. |
| 6,849,045 B2 | 2/2005 | Iliff |
| 6,850,965 B2 | 2/2005 | Allen |
| 6,856,809 B2 | 2/2005 | Fostick |
| 6,859,833 B2 | 2/2005 | Kirsch et al. |
| 6,910,035 B2 | 6/2005 | Hoekman et al. |
| 6,937,699 B1 | 8/2005 | Schuster et al. |
| 6,968,174 B1 | 11/2005 | Trandal et al. |
| 6,993,326 B2 | 1/2006 | Link, II et al. |
| 7,028,012 B2 | 4/2006 | St. Vrain |
| 7,035,381 B2 | 4/2006 | D'Ascenzo et al. |
| 7,035,468 B2 | 4/2006 | Yogeshwar et al. |
| 7,035,634 B2 | 4/2006 | Mead et al. |
| 7,076,037 B1 | 7/2006 | Gonen et al. |
| 7,092,901 B2 | 8/2006 | Davis et al. |
| 7,099,306 B2 | 8/2006 | Goodman et al. |
| 7,103,010 B2 | 9/2006 | Melideo |
| 7,120,235 B2 | 10/2006 | Altberg et al. |
| 7,181,415 B2 | 2/2007 | Blaser et al. |
| 7,187,761 B2 | 3/2007 | Bookstaff |
| 7,200,413 B2 | 4/2007 | Montemer |
| 7,212,615 B2 | 5/2007 | Wolmuth |
| 7,224,781 B2 | 5/2007 | Jacob et al. |
| 7,227,936 B2 | 6/2007 | Bookstaff |
| 7,231,405 B2 | 6/2007 | Xia |
| 7,240,110 B2 | 7/2007 | Haitsuka et al. |
| 7,240,290 B2 | 7/2007 | Melideo |
| 7,249,045 B2 | 7/2007 | Lauffer |
| 7,297,108 B2 | 11/2007 | Iliff |
| 7,297,111 B2 | 11/2007 | Iliff |
| 7,300,402 B2 | 11/2007 | Iliff |
| 7,306,560 B2 | 12/2007 | Iliff |
| 7,363,254 B2 | 4/2008 | Skinner |
| 7,366,683 B2 | 4/2008 | Altberg et al. |
| 7,380,139 B2 | 5/2008 | Tagawa et al. |
| 7,401,053 B2 | 7/2008 | Kamimura et al. |
| 7,433,459 B2 | 10/2008 | Reding |
| 7,434,175 B2 | 10/2008 | Melideo |
| 7,475,149 B2 | 1/2009 | Jacob |
| 7,630,919 B1 | 12/2009 | Obrecht |
| 7,729,938 B2 | 6/2010 | Lauffer |
| 8,396,735 B2 | 3/2013 | Lauffer |
| 2001/0012913 A1 | 8/2001 | Iliff |
| 2001/0027481 A1 | 10/2001 | Whyel |
| 2001/0032247 A1 | 10/2001 | Kanaya |
| 2001/0037283 A1 | 11/2001 | Mullaney |
| 2001/0048737 A1 | 12/2001 | Goldberg et al. |
| 2002/0003867 A1 | 1/2002 | Rothschild et al. |
| 2002/0010608 A1 | 1/2002 | Faber et al. |
| 2002/0010616 A1 | 1/2002 | Itzhaki |
| 2002/0026457 A1 | 2/2002 | Jensen |
| 2002/0038233 A1 | 3/2002 | Shubov et al. |
| 2002/0057776 A1 | 5/2002 | Dyer |
| 2002/0095331 A1 | 7/2002 | Osman et al. |

(56) References Cited

U.S. PATENT DOCUMENTS

| | | |
|---|---|---|
| 2002/0107697 A1 | 8/2002 | Jensen |
| 2002/0120554 A1 | 8/2002 | Vega |
| 2002/0122547 A1 | 9/2002 | Hinchey et al. |
| 2002/0133402 A1 | 9/2002 | Faber et al. |
| 2002/0136377 A1 | 9/2002 | Stewart et al. |
| 2002/0191762 A1 | 12/2002 | Benson |
| 2002/0193094 A1 | 12/2002 | Lawless et al. |
| 2003/0026397 A1 | 2/2003 | McCroskey |
| 2003/0046161 A1 | 3/2003 | Kamangar et al. |
| 2003/0050837 A1 | 3/2003 | Kim |
| 2003/0083042 A1 | 5/2003 | Abuhamdeh |
| 2003/0105824 A1 | 6/2003 | Brechner et al. |
| 2003/0195787 A1 | 10/2003 | Brunk et al. |
| 2003/0212600 A1 | 11/2003 | Hood et al. |
| 2003/0220866 A1 | 11/2003 | Pisaris-Henderson et al. |
| 2003/0223565 A1 | 12/2003 | Montemer |
| 2003/0225682 A1 | 12/2003 | Montemer |
| 2003/0231754 A1 | 12/2003 | Stein et al. |
| 2004/0003041 A1 | 1/2004 | Moore et al. |
| 2004/0006511 A1 | 1/2004 | Montemer |
| 2004/0010518 A1 | 1/2004 | Montemer |
| 2004/0076403 A1 | 4/2004 | Mankovitz |
| 2004/0083133 A1 | 4/2004 | Nicholas et al. |
| 2004/0162757 A1 | 8/2004 | Pisaris-Henderson |
| 2004/0174965 A1 | 9/2004 | Brahm et al. |
| 2004/0174974 A1 | 9/2004 | Meek et al. |
| 2004/0193488 A1 | 9/2004 | Khoo et al. |
| 2004/0234049 A1 | 11/2004 | Melideo |
| 2004/0235524 A1 | 11/2004 | Abuhamdeh |
| 2004/0247092 A1 | 12/2004 | Timmins et al. |
| 2004/0249649 A1 | 12/2004 | Stratton et al. |
| 2004/0249778 A1 | 12/2004 | Iliff |
| 2004/0254859 A1 | 12/2004 | Aslanian |
| 2004/0260413 A1 | 12/2004 | Melideo |
| 2005/0018829 A1 | 1/2005 | Baker |
| 2005/0041647 A1 | 2/2005 | Stinnie |
| 2005/0048961 A1 | 3/2005 | Ribaudo et al. |
| 2005/0065811 A1 | 3/2005 | Chu et al. |
| 2005/0074100 A1 | 4/2005 | Lederman |
| 2005/0076100 A1 | 4/2005 | Armstrong |
| 2005/0080878 A1 | 4/2005 | Cunningham et al. |
| 2005/0086104 A1 | 4/2005 | McFadden |
| 2005/0096980 A1 | 5/2005 | Koningstein |
| 2005/0100153 A1 | 5/2005 | Pines et al. |
| 2005/0105881 A1 | 5/2005 | Mankovitz |
| 2005/0114210 A1 | 5/2005 | Faber et al. |
| 2005/0125416 A1 | 6/2005 | Kirsch et al. |
| 2005/0135387 A1 | 6/2005 | Rychener et al. |
| 2005/0165666 A1 | 7/2005 | Wong et al. |
| 2005/0203799 A1 | 9/2005 | Faber et al. |
| 2005/0207432 A1 | 9/2005 | Velez-Rivera et al. |
| 2005/0209874 A1 | 9/2005 | Rossini |
| 2005/0216341 A1 | 9/2005 | Agarwal et al. |
| 2005/0222908 A1 | 10/2005 | Altberg et al. |
| 2005/0240432 A1 | 10/2005 | Jensen |
| 2005/0245241 A1 | 11/2005 | Durand et al. |
| 2005/0251445 A1 | 11/2005 | Wong et al. |
| 2005/0261964 A1 | 11/2005 | Fang |
| 2005/0286688 A1 | 12/2005 | Scherer |
| 2005/0289015 A1 | 12/2005 | Hunter et al. |
| 2006/0003735 A1 | 1/2006 | Trandal et al. |
| 2006/0004627 A1 | 1/2006 | Baluja |
| 2006/0069610 A1 | 3/2006 | Rossini |
| 2006/0095343 A1 | 5/2006 | Clarke et al. |
| 2006/0099936 A1 | 5/2006 | Link et al. |
| 2006/0106711 A1 | 5/2006 | Melideo |
| 2006/0136310 A1 | 6/2006 | Gonen et al. |
| 2006/0159063 A1 | 7/2006 | Kumar |
| 2006/0166655 A1 | 7/2006 | Montemer |
| 2006/0171520 A1 | 8/2006 | Kliger |
| 2006/0173827 A1 | 8/2006 | Kliger |
| 2006/0173915 A1 | 8/2006 | Kliger |
| 2006/0182250 A1 | 8/2006 | Melideo |
| 2006/0184417 A1 | 8/2006 | Van der Linden et al. |
| 2006/0200380 A1 | 9/2006 | Ho et al. |
| 2006/0247999 A1 | 11/2006 | Gonen et al. |
| 2006/0259365 A1 | 11/2006 | Agarwal et al. |
| 2006/0277108 A1 | 12/2006 | Altberg et al. |
| 2006/0277181 A1 | 12/2006 | Temple et al. |
| 2007/0011240 A1 | 1/2007 | Altberg et al. |
| 2007/0022011 A1 | 1/2007 | Altberg et al. |
| 2007/0038507 A1 | 2/2007 | Kumer |
| 2007/0067219 A1 | 3/2007 | Altberg et al. |
| 2007/0078717 A1 | 4/2007 | Ho et al. |
| 2007/0081662 A1 | 4/2007 | Altberg et al. |
| 2007/0083408 A1 | 4/2007 | Altberg et al. |
| 2007/0100956 A1 | 5/2007 | Kumer |
| 2007/0116217 A1 | 5/2007 | Altberg et al. |
| 2007/0121844 A1 | 5/2007 | Altberg et al. |
| 2007/0121845 A1 | 5/2007 | Altberg et al. |
| 2007/0121846 A1 | 5/2007 | Altberg et al. |
| 2007/0121847 A1 | 5/2007 | Faber et al. |
| 2007/0121848 A1 | 5/2007 | Faber et al. |
| 2007/0124206 A1 | 5/2007 | Faber et al. |
| 2007/0124207 A1 | 5/2007 | Faber et al. |
| 2007/0127650 A1 | 6/2007 | Altberg et al. |
| 2007/0129054 A1 | 6/2007 | Andronikov et al. |
| 2007/0130014 A1 | 6/2007 | Altberg et al. |
| 2007/0140451 A1 | 6/2007 | Altberg et al. |
| 2007/0143182 A1 | 6/2007 | Faber et al. |
| 2007/0255622 A1 | 11/2007 | Swix et al. |
| 2007/0269038 A1 | 11/2007 | Gonen et al. |
| 2009/0006174 A1 | 1/2009 | Lauffer |
| 2010/0208028 A1 | 8/2010 | Lauffer |

FOREIGN PATENT DOCUMENTS

| | | |
|---|---|---|
| JP | 09233441 | 9/1997 |
| JP | 09319812 | 12/1997 |
| WO | 9705733 | 2/1997 |
| WO | 9802835 | 1/1998 |
| WO | 9804061 | 1/1998 |
| WO | 9813765 | 4/1998 |
| WO | 9838558 | 9/1998 |
| WO | 9847295 | 10/1998 |
| WO | 9955066 | 10/1999 |
| WO | 0057326 | 9/2000 |
| WO | 0127825 | 4/2001 |
| WO | 0128141 | 4/2001 |
| WO | 0244870 | 6/2002 |
| WO | 2005040962 | 5/2005 |
| WO | 2005086980 | 9/2005 |
| WO | 2005101269 | 10/2005 |
| WO | 2005109287 | 11/2005 |
| WO | 2005109288 | 11/2005 |
| WO | 2005111887 | 11/2005 |
| WO | 2005111893 | 11/2005 |
| WO | 2006091966 | 8/2006 |
| WO | 2006091970 | 8/2006 |
| WO | 2007028173 | 3/2007 |
| WO | 2007038618 | 4/2007 |

OTHER PUBLICATIONS

International Application No. PCT/US05/12061, Written Opinion and International Search Report, Nov. 17, 2006.

"Sell and Buy Advice Online," The Ottawa Citizen, p. D7, Nov. 29, 1999.

Bazini, Liz, "UpSnap Selects LookSmart to Sell Premium Listings on Free 411 Service for Text-Enabled Cell Phones," Nov. 4, 2004.

Becker, Ralph, "ISDN Tutorial: Interfaces," retrieved from http://www.ralphb.net/ISDN/ifaces.html, available at least by Apr. 21, 2000.

Chimiak, William H. et al., "Multimedia Collaborative Remote Consultation Tools via Gigabit WAN in Teleradiology," IEEE 13th Annual International Phoenix Conference on Computers and Communications, pp. 417-423, Apr. 12-15, 1994.

Clark, Don, "Keen.com Plans Web Service Allowing Customers to Hold Private Phone Chats," Wall Street Journal, Nov. 8, 1999.

De Lasser, Eleena, "When Business Plan and Real World Clash," Wall Street Journal, p. B1, Jun. 1999.

(56) References Cited

OTHER PUBLICATIONS

Drescher, Bob et al., "Aspect Telecommunications Integrates the Web into the Call Center to Deliver New Level of Customer Service," Business Wire, Aug. 5, 1996.
Dyson, Esther, "Information, Bid and Asked," Forbes, p. 92, Aug. 20, 1990.
Ellis, James E., "For Telesphere's Clients, Dial 1-900 TUF LUCK," Business Week, pp. 88-89, Sep. 9, 1991.
Green Digital Media, Inc., Big Green Blog: Jan. 2005 Archives, Jan. 28-31, 2005.
Griffiths, J.W.R. et al., "Multimedia Communication in a Medical Environment," Singapore International Conference on Networks, pp. 166-171, Sep. 5, 1991.
Herman, Edith, "U.S. Courts to Launch First Federal 900 Service," Federal Computer Week, pp. 8, 10, Sep. 28, 1992.
Herzberg, Amir et al., "MiniPay: Charging Per Click on the Web," Computer Networks and ISDN Systems, vol. 29, pp. 939-951, Sep. 1997.
Ingenio, Inc., "Keen: Your Personal Advisor," retrieved from http://www.keen.com, available at least by Feb. 4, 2006.
Ingenio, Inc., Press Archives for 2004, retrieved from http://www.ingenio.com on Feb. 21, 2006.
International Application No. PCT/US01/48284, International Search Report, May 13, 2002.
Jarvie, Barbara, "Company Devoted to Hot-Line Support," Computer Reseller News, p. 48, Oct. 21, 1991.
Kuehn, Richard A., "The Voice of Technology," Credit World, pp. 20-23, Jul. 1994.
Melideo, John, U.S. Appl. No. 60/471,535 entitled "HyperDial," filed May 19, 2003.
Mercalli, Franco et al., "The ESSAI Teleshopping System: An Example of a Broadband Multimedia Application," IEEE Global Telecommunications Conference, pp. 572-576, Nov. 28, 1994.
Reding, Craig et al., U.S. Appl. No. 09/596,466 entitled "Methods and Apparatus for Providing Telephone Support for Internet Sales," filed Jun. 19, 2000.
Robinson, John, "Attachmate Ready to Answer 'Net Questions," Network World, p. 37, Apr. 8, 1996.
Sairamesh, Jakka et al., "NetBazaar: Networked Electronic Markets for Trading Computation and Information Services," Second European Conference on Research and Advanced Technology for Digital Libraries, pp. 839-856, Sep. 21, 1998.
Telecommunications Buyers Guide and Directory, Editor & Publisher, pp. 29TC-38TC, Feb. 12, 1994.
U.S. District Court, Southern District of New York, *Keen.com, Inc.* v. *InfoRocket.com, Inc.*, Preliminary Injunction Hearing, pp. 286-289, Jan. 8, 2002.
U.S. District Court, Southern District of New York, *Keen.com, Inc.* v. *InfoRocket.com, Inc.*: Complaint for Patent Infringement, Trade Dress Infringement and Unfair Competition; Demand for Jury Trial, Aug. 31, 2001.
Wagner, Mary, "Caring for Customers: Real-Time Text Chat and Telephony Provide Personalized Customer Support and Turn Queries into Sales Leads," Internet World Media, vol. 5, iss. 28, p. 30, Sep. 1, 1999.
Wood, Christina, "Hidden Cost of Tech Support," PC World, pp. 143-152, 156, May 1995.
Rogers, Michael et al., "Experts Abound at New Web Sites," Library Journal, pp. 22-24, Mar. 1, 2000.
Tehrani, Rich, "e-Rip Van Winkle and the 60-second Nap," Call Center Solutions, vol. 18, No. 2, pp. 16-18, Aug. 1999.
"AtOnce Talks Up E-mail Marketing Campaigns with ITXC Push to Talk Service," Business Wire, Feb. 26, 2001.
"ITXC Corp and Doubleclick Energize Banner Ads with Web Telephony; Companies Voice-Enable Banner Advertisements Using ITXC Push to Talk Service," Business Wire, Dec. 12, 2000.
ADS-Click, "ADS-click Adds Skype-Based Pay-Per-Call Advertising Capabilities to Its Private-Labeled Solution, which will be Unveiled at ad:tech New York," Market Wire, Oct. 10, 2005.
Greenberg, Ken, "Jambo Names Netzero Co-founder Stacy Haitsuka to New Post of Chief Information Officer," Business Wire, Jul. 5, 2005.
Greenberg, Ken, "Jambo Receives $5 Million in Financing from Kline Hawkes & Co., Westlake Venture Partners, Others," Business Wire, Oct. 17, 2005.
Ingenio, Inc., "FindWhat.com Enters Agreement with Ingenio to Offer Pay Per Call Advertising Platform," press release available at http://www.ingenio.com, Apr. 7, 2004.
Jambo, "Welcome to Jambo—The Leader in Pay-Per-Call Solutions," company information retrieved from http://www.jambo.com, available at least by Oct. 17, 2005.
Jingle Networks, Inc., "1-800-FREE411 Provides Two Great Opportunities to Acquire New Customers," available at least by Oct. 20, 2005.
Jingle Networks, Inc., "Introducing 1-800 FREE411: First Nationwide Free Telephone Directory Assistance Service," Sep. 20, 2005.
"Applying Technology News," Accounting Technology, p. 14, Feb./Mar. 1997.
"TriNet's 'Help Me, I'm Stuck' Internet Voice Button Services Pushes Web Pages to Online Users," Business Wire, Mar. 25, 1998.
allexperts.com, company information retrieved from http://lwww.allexperts.com, available at least by Apr. 9, 2000.
answers.com, company information retrieved from http://www.answers.com, available at least by Aug. 8, 2000.
Dalton, Gregory, "Rent-An-Expert on the Web," Information Week, p. 75, Sep. 6, 1999.
exp.com, Inc., company information retrieved from http://www.exp.com, available at least by Sep. 20, 2000.
expertcity.com, "About Us," company information retrieved from http://www.expertcity.com, available at least by Apr. 9, 2000.
Experts Exchange, Inc., company information retrieved from http://www.experts-exchange.com, available at least by Apr. 9, 2000.
University of Texas—Austin, information on the Electronic Emissary Project retrieved at www.tapr.org/emissary, available at least by Apr. 9, 2000.
Wasik, Joann M., "Information for Sale: Commercial Digital Reference and AskA Services," Virtual Reference Desk, http://www.vrd.org/AskA/commAskA.html, Sep. 20, 1999.
Wieland, Heidi et al., "Expertcity.com Launches Premier Online Marketplace for Expert Services," PR Newswire, Aug. 30, 1999.
"Connecting to On-Line Car Shoppers: Auto Sellers Use Netcall Internet Call-Button Technology to Turn 'Clicks' into Interactive Sales," Business Wire, p. 4089, Jul. 19, 1999.
"Keen.com raises $60 Million from Prestigious Investors and Strategic Partners Just 60 Days After Launch of Its Live Answer Community," Business Wire, Jan. 11, 2000.
"NetCall Internet Call Buttons Enhance E-Commerce Customer Service and Sales," PR Newswire, p. 7431, Aug. 9, 1999.
Addeo, E.J. et al., "An Experimental Multi-Media Bridging System," Frontiers in Computer Communications Technology, Computer Communications Review, vol. 17, No. 5, pp. 236-242, Aug. 11-13, 1987.
Angelo, Simon, "SurfBrains.com: Brains Online Save Time & Money," M2 Presswire, Jul. 11, 2000.
Asthana, Abhaya et al., "A Small Domain Communications System for Personalized Shopping Assistance," IEEE International Conference on Personal Wireless Communications, Publication No. 0-7803-1996-6/94, pp. 199-203, Aug. 18, 1994.
Becker, Ralph, "ISDN Tutorial: Definitions," retrieved from http://www.ralphb.net/ISDN/defs.html, available at least by Apr. 21, 2000.
Broad, Doug et al., "Lucent Technology and Netscape Team to Deliver Lucent Ecommerce Solutions," Business Wire, Sep. 23, 1998.
Collett, Stacey et al., "Why Online Browsers Don't Become Buyers," Computerworld, vol. 33, No. 48, p. 14, Nov. 29, 1999.
Davey, Tom, "Wheeling and Dealing Online," PC Week, vol. 13, No. 45, pp. 1, 129, Nov. 11, 1996.
Ek, Brian, "Walker Digital Issued Landmark U.S. Patent No. 5,862,223 for Global Internet Marketplace for Experts", Business Wire, Jan. 26, 1999.
Greenblatt, Ellen, "Have You Ever Wondered . . . ," Datamation, p. 126, Oct. 1997.

(56) References Cited

OTHER PUBLICATIONS

Hase, Masahiko et al., "Advanced Videophone System Using Synchronized Video Filing Equipment," NTT Review, vol. 3, No. 4, pp. 29-36, Jul. 1991.

Healey, John, "From A-Z: You Can Sell Advice Online," San Jose Mercury News, retrieved from http://www.mercurycenter.com on Oct. 24, 2001.

Hodgson, Cynthia, "Online Expert Databases & Services," Econtent, pp. 48-53, Dec. 1999.

Information Markets Corp., company information retrieved from http://www.infomarkets.com, available at least by Aug. 8, 2000.

About intellectexchange.com, Inc., company information retrieved from http://www.intellectexchange.com/About.asp, pp. 1-12, available at least by Aug. 8, 2000.

International Application No. PCT/US00/06849, International Search Report, May 16, 2000.

International Application No. PCT/US00/10730, International Search Report, Jan. 3, 2001.

Kabeya, Kiyoshi et al., "A New Teleconsultation Terminal System Using ISDN," NTT Review, vol. 3, No. 4, pp. 37-43, Jul. 1991.

Kanellos, Michael, "WebWatch: Do You Want to Know the Meaning of Life?," Computer Reseller News, pp. 72-74, Mar. 3, 1997.

keen.com, "Keen.Com Launches First Live Answer Community, Connects People with Information to Share Over Their Standard Telephone," company press release, Nov. 8, 1999.

keen.com, company information retrieved from http://www.keen.com, available at least by 1999.

Littleton, Linda, "HDD: A Helpdesk Database," Proceedings of the ACM SIGUCCS User Services Conference XXII, pp. 205-210, Oct. 16-19, 1994.

Ludwig, L.F. et al., "Laboratory for Emulation and Study of Integrated and Coordinated Media Communication," Conference on Office Information Systems, pp. 283-291, Mar. 23-25, 1988.

Menn, Joseph, "An Expert? There's Now a Home for You on the Internet," Los Angeles Times, retrieved from http://www.denverpost.com on Oct. 24, 2001.

Moore, Michael et al., "USA Global Link Brings Interactively to Internet Shopping," Business Wire, Oct. 7, 1998.

Ott, Chris, "Making Good on the Information Economy," Denver Business Journal, vol. 51, No. 17, p. 27A, Dec. 17, 1999.

Pelline, Jeff, "Net Firm to Connect Users by Phone," CNET News.com, Nov. 8, 1999.

qcircuit.com, company information retrieved from http://www.qcircuit.com, available at least by Aug. 8, 2000.

\* cited by examiner

Diverse Advice Sources

Compensation for Advice:

Information Flow:

METHOD AND SYSTEM TO CONNECT CONSUMERS TO INFORMATION

CROSS REFERENCE TO RELATED APPLICATIONS

The present application is a continuation application of U.S. patent application Ser. No. 12/768,664, filed Apr. 27, 2010, which is a continuation application of U.S. patent application Ser. No. 11/772,525, filed Jul. 2, 2007 and now U.S. Pat. No. 7,729,938, which is a continuation application of U.S. patent application Ser. No. 10/951,502, filed Sep. 27, 2004 and now U.S. Pat. No. 7,249,045, which is a continuation application of U.S. patent application Ser. No. 10/107,743, filed Mar. 26, 2002 and now U.S. Pat. No. 6,801,899, which is a continuation of U.S. patent application Ser. No. 09/488,130, filed Jan. 20, 2000 and now U.S. Pat. No. 6,223,165, which claims the benefit of Provisional U.S. Patent Application Ser. No. 60/125,557, filed Mar. 22, 1999, the disclosures of which are incorporated herein by reference.

FIELD OF THE INVENTION

The present invention relates to techniques for delivering information electronically, more particularly, for delivering advice to consumers from a diverse set of experts. Still more particularly, the present invention relates to systems and methods for matching consumers questions with experts, displaying available experts for consumer viewing and selection, providing for compensation from consumers to experts, and providing for the connection between consumer and experts.

Definitions

Advice: Any needs of the consumer which can be provided for by an expert, including but not limited to conversation, entertainment, sounds or pictures of any kind, text, video, audio. This advice is not limited to that provided by agents regarding company products; it can include medical, legal, educational, travel, entertainment, religious, and other forms of advice. In addition, herein "advice" is meant broadly to include any type of information, comfort, or communication a consumer desires.

Consumers: Individuals, companies, organizations, governments, or devices which have one or more questions or needs for advice.

Experts: Individuals, companies, organizations, governments, or devices which are able to provide advice to consumers, provided that experts' initial means to contact consumers is via the server in the Advice Router. Experts' compensation, which may be zero, can come from either consumers directly or from the Advice Router. Collectively, experts represent a broader range of knowledge and experience than do agents which work for a single company. Much as the word "advice" is used broadly, "expert" is meant broadly-since-many types of information can be given by human beings.

Agents: Individuals, companies, organizations, governments, or devices who, as part of their relationship/employment at that institution, answers questions when connected to his institution's telephone or server, provided that the agent is paid by the institution for that function. The advice provided for by agents is generally restricted to that regarding products offered by their respective company.

Server: any device, network or software which connects consumers and experts.

Query: an action initiated by a consumer which includes keywords or other means to summarize their question or need for advice.

Expert characteristics: used for matching with consumers queries. Including, but not limited to one or more of the following: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1, 2, 5, 10, 15, 30, 60 minutes.

Matching: a process for scoring and putting in an order of relevance a list or selected list of experts who are likely to be able to answer a consumer's query. Can involve any method of assignment of numbers to the number of keyword matches or matches between ranges of characteristics desired by the consumer with the actual expert characteristics.

Logged in, or on-line: detectable means of communication between server and expert, including but not limited to telephone, Internet telephony, email, audio, and/or video.

Means to contact: any method, information, or technology used to bring together the consumer with one or more experts, including but not limited to telephone, Internet telephony, email, audio, and/or video. Means to contact includes telephone numbers (including toll-free and pay-per-call numbers), email addresses, Internet web pages or sites, videoconferencing details. More preferably, the means of contact includes telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

Time-to-connect: the period of time between the transmission of the means of contact and the actual connection between expert and consumer. In the case where the consumer selects an expert, the time-to-connect is the period of time beginning when at the consumer's last action (e.g., clicking on the symbol for an expert or his telephone number) and ending when the actual connection is made. In the case where the server makes both connections, the time-to-connect is the period of time beginning when the server indicates to the consumer that it is beginning to contact the expert and ending when the actual connection is made.

BRIEF DESCRIPTION OF THE FIGURES

FIG. 1.b shows a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. This technology is in an hourglass shape where a large number of experts is available rather than the small number of agents at each company. In the middle is a new form of information company, the Advice Router, which rapidly facilitates the matching of and connection between consumers and experts.

BACKGROUND

Problems with Customer Service and General Advice

As more technology (videorecorders, personal computers, Internet, TV web boxes, cell phones, etc.) enters peoples' lives, there is greater and greater demand for help in choosing devices and solutions and in setting them up and correcting problems. Even more generally, there is greater need for assistance in daily life, whether it is for medical, legal, family, or entertainment reasons.

At the same time that more information is required to conduct our lives, available effective sources of that information have not grown sufficiency in number or efficiency.

Companies selling products often have web pages or telephone support lines, but these are either too restricted in information, or the consumer must wait for long periods for live help.

To help with the routing of calls to available agents in a company, Cave (WO9813765) has devised a real-time system wherein a queuing manager routes calls to an agent who is free at the time. The system still involves automated answering systems which many consumers find frustrating, and it requires the hiring of not only agents but the queuing manager.

In the future, streaming audio and video capabilities on the web will make it possible for company agents to speak directly to consumers. However, this will be very costly to operate and the consumer will probably have to wait for long times to speak to one of the agents.

For general advice, the Internet is far too inefficient for many uses. Search engines return many hits, requiring the consumer to try many web sites and hope that the answer is available.

1-900 phone numbers (pay-per-call) are limited in scope and consumers hesitate to use them due to high per-minute rates, lack of trust in the billing, and generally perceived notions that the 900 numbers are for less-than-serious concerns such as astrology or sex chat. In addition, 900 services are small and narrowly focused, without the benefits of the Diverse Advice Sources arrangement, and they did not include matching and/or display technologies.

Figure 1A:
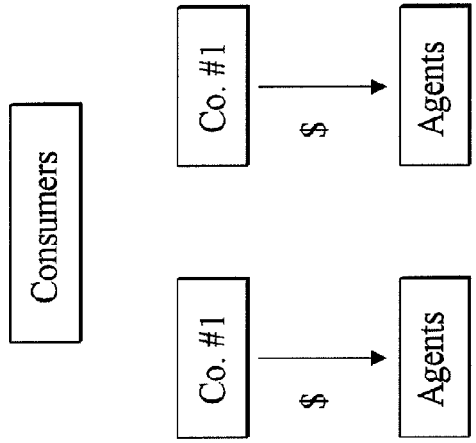
FIG. 1.a shows the most common arrangement today of the advice business, known as Centralized Advice Sources, where there are a large number of consumers and few agents to help them at each company; this has the general shape of a funnel with too many questions going to too few agents.
Figure 1A:
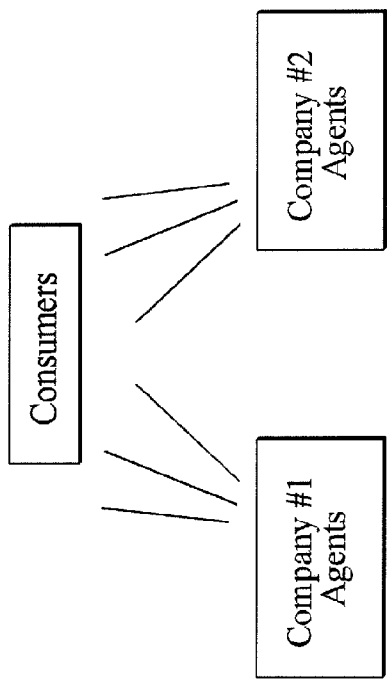
Figure 1B:
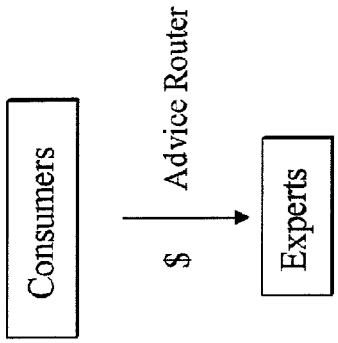
Figure 1B:
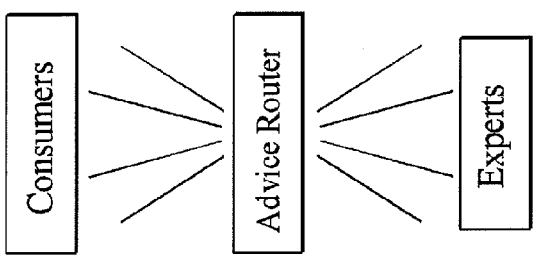

As shown in FIG. 1.a, the fundamental problem with current advice technologies is that there are a large number of consumers and few agents to help them at each company; this is known as Centralized Advice Sources, and the has the general shape of a funnel with too many questions going to too few agents. This leads to high cost (to pay agents and purchase systems), slow response time (long hold times on telephone), and lack of personal service (live agents). In addition, the agents often can only answer a limited range of questions regarding the companies products. Thus, the participation and control of the consumer advice function by each company is fundamentally hurting the company by frustrating consumers and by requiring it to staff, manage, and pay for a vast and complex undertaking which is, outside of its main expertise (making widgets, providing a narrow service, etc.).

Previous solutions have not adequately filled the need, particularly for immediate advice or connection between appropriate people.

The American Information Exchange (AMIX) was a central exchange that attempted to mediate between buyers and sellers of information. But the complexity and lack of immediacy, among other problems, limited its ability to efficiently solve the buyer's problem.

Walker (U.S. Pat. No. 5,862,223) envisioned a similarly complex exchange, often involving several lengthy steps where a user request is submitted; a search of experts, even beyond its members, is undertaken; a portion of the user request (question) is transmitted to the computer-selected expert, etc. until the request if fulfilled. Walker (col 8, line 49; col 24, line 67) allows the user himself to select the expert from a general list, but there is no provision for seeing which expert is available at that instant to talk, and there is no provision to make the process of connecting the expert and user quickly, say within 1 min or 10 seconds. In addition the user must submit a portion of his question (end user request).

In the complex process described by Walker, the expert and user can communicate in real-time (col 9, line 1; col 26, line 49), but only after the process of submitting the end user request to the expert.

In another embodiment of Walker (col 28, line 66), the end user calls the central controller and eventually is put in touch with an expert for a real-time connection. No allowance is made for the central controller to make two separate calls (thus connecting the expert and user) after the user selects the expert.

In addition, there are no constraints in Walker on how fast the time-to-connect process needs to be to be useful. Timely information is more highly valued than delayed information.

Moreover, the detailed lists of experts and their characteristics (resumes, etc.) that are displayed in Walker (col 25, line 35) are not suitable for a system that fills the need for rapid selection and connection between parties; as the number of experts grows, there will be simply too many pages of text to scroll through. There is needed a new display system where users can rapidly survey the available experts via information-rich graphics.

Walker does not take into account the use of experts as a workforce for customer support. No mention is made of product or service companies issuing certification for experts, and, in turn, those certifications listed or displayed explicitly by the central controller/server.

DESCRIPTION

In one embodiment, this invention provides for a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. As shown in FIG. 1.b this technology is in an hourglass shape where a large number of experts is available rather than the small number of agents at each company. In the middle is a new form of information company, the Advice Router, which rapidly facilitates the matching of and connection between consumers and experts.

The sheer number of experts available in Diverse Advice Sources solves the arithmatic (funnel) problem of Centralized Advice Sources, leading to the two most important benefits: fast response and the routine availability of live experts. In addition the diversity of sources raises the likelihood that the consumer will get more holistic advice, not limited to the tools available from any one company.

In another embodiment, this invention provides for a method of (or apparatus for) facilitating the delivery of advice to consumers, comprising:

providing a server unit with the ability to store the names or identification of two or more experts, said experts coded by one or more expert characteristics, said server having the ability to detect which experts are online;

said server having the ability to display at least one of said expert characteristics with information-rich graphics or symbols;

said server having the ability to respond to a consumer's selection of expert by either sending the consumer a means to contact expert or by connecting the consumer and expert for real-time communication;

wherein the time-to-connect between consumer and expert is 30 minutes or less.

In another embodiment, this invention provides for a method of (or apparatus for) facilitating the delivery of advice to consumers, comprising:

providing a server unit with the ability to store the names or identification of two or more experts, said experts coded by one or more expert characteristics, said server having the ability to detect which experts are online;

said server unit having the ability to receive one or more keywords from a consumer;

said server unit having the ability to match those keywords to one or more experts and send the consumer a means to contact;

wherein the time-to-connect between consumer and expert is 30 minutes or less.

Certification

In the transition from central to diverse advice sources, companies will find that it is economical to broaden its customer support workforce to non-employees. While these non-employees may not have as detailed or as frequent training, they can answer many of the questions consumers have. Thus a company can offer simple tests and, optionally, transmit the results of those tests to the server, which maintains an up-to-date status of each expert. Alternatively, the company can simply give the certification to the expert who transmits the results to the server.

Certification tests can take many forms, including but not limited to web-based questionnaires, phone, Internet, or face-to-face interviews, live video connections, etc. Optionally, a company can use authentication procedures (fingerprint, voiceprint, "cookies" the expert's computer, passwords, etc.) to ensure the expert's identity. Optionally, the test and results can be cryptographically transmitted between the company and expert; or between the company and server.

Certification can also come from organizations or schools or governments.

Matching

In another embodiment, this invention provides for a matching system or relevance scoring method which finds the best expert to answer a consumer's question. This can involve any method of assignment of numbers to the number of keyword matches or matches between ranges of characteristics desired by the consumer with the actual expert characteristics. This technology is well known for search engines like Yahoo! for finding matches between a consumer's keywords and web pages as well as eBay for finding matches for merchandise. However, a system and method does not currently exist that allows one to match a wide array of features, including, but not limited to, two or more of the following expert characteristics: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1, 2, 5, 10, 15, 30, 60 minutes.

It is preferred that the number of categories in the list of expert characteristics used for matching be at least four, such as code name, keywords, compensation rate, and time availability. More preferably, the number of categories should be at least six. Even more preferably, the number of categories should be at least eight. Most preferred, the number of categories should be at least ten.

In another embodiment, this invention provides for a system for and method of displaying selected experts to the consumer. This includes, at a minimum, conveying, through means that include but are not limited to telephone, Internet telephony, email, audio, and/or video, a way for the consumer to contact the expert (the means of contact). It is more preferred for that conveyance to be performed by Internet telephony, email, audio, and/or video. It is most preferred for that conveyance to be performed by audio, and/or video.

The number of experts presented to the consumer can be at least one. It is more preferred that the number of experts presented to the consumer is at least two. It is even more preferred that the number of experts presented to the consumer is at least five. It is even more preferred that the number of experts presented to the consumer is at least ten. It is even more preferred that the number of experts presented to the consumer is at least 20. It is most preferred that the number of experts presented to the consumer is over 100.

In another embodiment, this invention provides for a system for and method of protecting the privacy and identity of both the expert and the consumer. If the expert prefers, his actual name, address and other information will be withheld from the consumer. Also, individual entries in the expert characteristics list can be shielded from view by the consumer. The consumer likewise can be protected. While privacy has been provided for in commercial/advertising technologies (see Goldhaber, U.S. Pat. No. 5,855,008), the shielding but still utilizing detailed expert characteristic lists has not been provided for.

Display

In addition to the mere conveyance of the means of contact, it is more preferred for the consumer to be presented with a visual display of available experts. Systems and methods have been used by Yahoo! and others for displaying game-playing individuals, with information related to availability for a game now, skill level, and code name. No such system or method exists for displaying expert characteristics.

Display methods include but are not limited to information-rich graphics such as objects with varying color or density, bar graphs, line graphs, 3-D graphs, icons, pictures, photographs, video. All of the above can include animation or motion to attract attention. Words and numbers can be added on or near any of the above to give further expert characteristics. Any of the above can be addressable by mouse/cursor location so that the consumer can easily select which expert to choose or which set of experts to zoom in on and view more closely. Optionally, zoom (magnification) and/or rotation functions can also be used. The zoom function can allow new and more detailed expert characteristics to appear with each increase in magnification. Similarly rotations of objects can reveal more detailed expert characteristics.

Useful expert characteristics that can be displayed visually include, but are not limited to: the expert's quality (rating) score, whether the expert is online now, or how long until he will be; whether the expert has a separate phone line, and whether it is busy or not.

A legend can optionally be provided when abstract symbols or colors are used so that consumers can tell what each symbol or color means.

In another embodiment, experts can select their own symbol, pictures, logos, etc. to advertise themselves (as advertisers). These include all of the above options. Optionally, they can use online avatars to represent themselves, with the additional option of the voice and facial expression of the expert transmitted to the consumer via this avatar.

In another embodiment, a special symbol/notation is displayed next to or as part of an experts symbol if he has been certified by selected companies or organizations. The symbol/notation can optionally expire, disappear, or change its characteristics (color, etc.) after a certain length of time so that the expert is forced to take tests to maintain certification.

In another embodiment, the display is a map either of geography, system or building architecture or any type of display where experts are, at that time, located or qualified in. The map and expert symbols on it is continually updated to see who is online and/or their exact or general location. The size of the symbol used for each expert is adjusted as the number of experts online increases so each can be displayed. Optionally the zoom function allows better viewing of crowded regions of the map.

This display method can be useful in cases where a consumer only wants information from someone at a particular location, e.g., to determine weather, sport conditions (ski, surf, etc), traffic, delivery/pickup truck availability, nature (animal sightings), entertainment (club-hopping), state or city laws, or any kind of location-dependent information.

Other types of non-geographical maps or diagrams can also be used, including but not limited to software architecture, flow charts, graphs, etc. Here the location of the expert's symbol is determined by their expertise in a particular subject within that map.

In some cases, if the expert is qualified in more than one area, two or more of his symbols may appear in a given map or diagram.

Graphical displays (line or scatter plots, etc) can be used by the consumer to weigh different features of the experts before making a selection. The consumer can be given a choice of 2- or 3-dimensional, and what the axis of the graph represent: quality score, compensation rate, distance from the consumer, etc. The symbols for the available experts in a particular subject area are placed in their appropriate position of the graph and the consumer can see, for example a scattergram and pick a well-rated expert who is not too expensive.

It is more preferred that the display method graphically show at least the following two items: relevance score or order of preference of experts on the one hand, and the time availability of the expert on the other. The latter refers to whether the expert is available at the actual moment of consumers query or within 1, 2, 5, 10, 15, 30, 60 minutes. It is even more preferred that the display method graphically show at least the following three items: relevance score or order of preference of expert, the time availability of the expert, and the compensation rate for consumer advice with that expert. It is even more preferred that the display method graphically show at least the following four items: relevance score or order of preference of expert, the time availability of the expert, the compensation rate for consumer advice with that expert and the quality score as judged by previous consumer interactions. It is most preferred that the display method graphically show at least the following five items: relevance score or order of preference of expert, the time availability of the expert, the compensation rate for consumer advice with that expert, the quality score as judged by previous consumer interactions, and one item selected from the following list: number of years experience in each area of expertise; degrees earned; number of years of school after completion of high school or college; companies worked for or schools/training programs attended in the past or present; age; language; neighborhood, city, state, and/or country of residence.

Compensation

Diverse Advice Sources fundamentally changes the economics of the consumer advice business. As shown in FIG. 1, Diverse Advice Sources replaces the awkward arrangement in Centralized Advice Sources wherein individual companies are expected to pay for consumer advice (by paying their hired agents) when it is the consumer who is benefiting from the advice. Of course consumers had in the past expected companies to pay for this advice, to encourage the consumer to use their product and not products from competing companies. The companies respond by establishing limited consumer advice groups which are highly inefficient and costly to the company. In Diverse Advice Sources, the consumer pays for the advice information packet directly, to either or both of the expert and the Advice Router.

This invention also includes an alternative case where the consumer does not directly pay either the expert or the Advice Router. In this special case, general advertisements are used to fund the Advice Router, and the Advice Router either compensates the expert for his time, or the expert receives no direct compensation and instead gains some other value (e.g., advertising).

Unique payment systems and methods used by the Advice Router include but are not limited to the following:

a) credit card or (cyber-money) accounts for one or both of the consumer and expert; proper deductions and credits are made to each account after each transaction.

b) the means of contact can include a 900 number (or similar per-per-call/pay-per-view technology for the Internet); in this case, the consumer simply dials the 900 number given by and controlled or contracted for by the Advice Router, and the expert is paid according to well-known 900 number technology. This 900 number technology has been used in the past to provide advice from individual groups, but these activities did not include matching and/or display technologies, nor did they have the benefits of the Diverse Advice Sources arrangement.

c) other phone or media accounts.

Various payment schemes can be optimized to meet consumer and expert expectations. For example, rather that a flat per-hour, per-minute, or per-session rate, a number of schemes can be used to compensate for the consumer ensuring that the expert is adequate (for example, the first two minutes free), etc.

In all of these cases, the Advice Router can receive a fee for conveying the means of contact, and/or the connection.

Also, the Advice Router can pay or rebate a portion of the consumer charge if the consumer take some additional action, such as rating the quality of the expert, etc.

Connection

This invention provides for a system and method whereby the server used by the Advice Router can be used for providing for or aiding rapid connections and monitoring of interactions between consumers and experts.

Regarding the connection, it is preferred that the server provide for or facilitate a connection within 30 minutes after the means of contact has been conveyed to the consumer. It is more preferred that the time-to-connect is 10 minutes or less. It is even more preferred that the time-to-connect is 5 minutes or less. It is even more preferred that the time-to-connect is 2 minutes or less. It is even more preferred that the time-to-connect is 1 minute or less. It is even more preferred that the time-to-connect is 30 seconds or less. It is even more preferred that the time-to-connect is 20 seconds or less. It is most preferred that the time-to-connect is 10 seconds or less.

The connection can include any method or technology used to bring together the consumer with one or more experts, including but not limited to telephone, Internet telephony, email, audio, and/or video. More preferably, the connection involves telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

In the case where the consumer selects an expert on the Internet, the server can connect both using a two-step procedure wherein two separate and independent transmissions (e.g., telephone calls) are placed and then the two transmissions are joined together. This allows the server to store the expert addresses/phone numbers anonymously and control the connection.

The server should be able to monitor the interactions to provide for quality control and/or exact payment.

EXAMPLE

Two experts, Joe and Bill, connect to the Advice Router and fill out forms describing their expertise. Joe is expert in Microsoft's Word and Powerpoint programs, and Bill is expert in the Word and Excel programs. The server detects that they are both logged on. Later that evening, Bill is busy with a consumer for a period he estimates will be 15 more minutes. Joe is free. At that moment, David, a consumer, logs on and fills out a keyword query list that best suits his question: how to turn off the automatic spellchecker in Microsoft Word. He also gives his VISA credit card number via a secure link. A second after he finishes his entry, a display on his PC shows two color-coded boxes coinciding with the current list of available experts, Joe and Bill (only their code names are used, however). The relevance score for both is 1.0 (optimal) since both are experts in Microsoft Word. Both experts also charge the same rate, $1.00 per minute. However, a small box in Joe's area is clearly green and easy to read—this box corresponds to the fact that Joe is available at this instant to speak to David. (David does not select Bill since the red color in his box corresponds to a 15 min. wait or more.) David clicks an icon in Joe's box and a second or two later, a streaming real-time video of Joe appears on David's PC, and if David's PC is so enabled, Joe sees David in his PC. They spend five minutes solving David's problem and log out. Prior to logging out, however, David receives a $0.50 rebate on the cost of the connection by rating the quality of Joe's help, from 0 for "awful" to 10 for "great." The cost of David's call is $5.00 minus $0.50 or $4.50; in his case, this is added to his monthly $50-$100 phone/Internet bill.

For maintaining the site, the Advice Router deducts $1.00 from the net $4.50 received and remits $3.50 to Joe. If David had not elected to receive the $0.50 rebate, the Advice Router would have made $1.50 on the call.

For most of its experts, the Advice Router takes out 30% before paying the experts.

Those skilled in the art will know that this example is illustrative only and does not in any way limit the range of applications of the present invention.

What is claimed is:

1. A non-transitory machine-readable medium having stored thereon a set of instructions, which when executed by a server system causes the server system to perform a method, the method comprising:

transmitting, by the server system to an end-user computing device via an Internet, a web page configured to indicate an option to receive, from a user, a request via the web page and a browser of the end-user computing device;

processing, by the server system, a first indication of a selection of the option;

selecting, by the server system, an advisor from a plurality of advisors for indication in an advertisement for the advisor, the selecting based at least in part on a compensation rate of the advisor and a quality score of the advisor;

determining, by the server system, a status of the advisor;

in response to the selection, transmitting to the end-user computing device the advertisement for the advisor, the advertisement to be visually displayed via the end-user computing device, wherein the advertisement includes:

at least one reference selectable by the user to request a real-time communication connection with the advisor, wherein the real-time communication connection is separate from an Internet connection used by the end-user computing device to download the web page; and an indication of the status of the advisor;

while the advisor is determined to be currently available for real-time communication, receiving, by the server system, from the end-user computing device a second indication of a user selection of the at least one reference made via the advertisement, the user selection of the at least one reference corresponding to the advisor; and in response to the second indication of the user selection of the at least one reference, establishing a telephonic connection via a central controller of the server system to provide the real-time communication connection requested between the advisor and the user, wherein the establishing the telephonic connection comprises the central controller directing a first transmission to the user, the central controller directing a second transmission to the advisor, and the central controller joining the first transmission and the second transmission, and wherein the telephonic connection is separate from the Internet connection used by the end-user computing device to download the web page.

2. The medium of claim 1, wherein the method further comprises:

providing visual display of advertisements on a media channel on behalf of multiple advertisers, the visual display of advertisements to include the at least one reference for telephonic connections with respective advertisers of the multiple advertisers; and charging an amount each time a respective telephonic connection is established between a respective advertiser and a customer.

3. The medium of claim 1, wherein the transmitting the advertisement is in response to a search submitted by the user.

4. The medium of claim 3, wherein the search submitted by the user indicates a geographic location.

5. The medium of claim 3, wherein the search submitted by the user indicates a subject matter.

6. The medium of claim 3, wherein the search submitted by the user comprises a keyword search.

7. The medium of claim 1, wherein the method further comprises:

charging an amount for each telephonic connection established between the advisor and the user based on the advertisement.

8. The medium of claim 7, wherein the charging of the amount comprises deducting the amount from an amount received from the user.

9. The medium of claim 7, wherein the charging of the amount comprises charging the user.

10. The medium of claim 7, wherein the amount charged is according to a price specified by the advisor.

11. A server system, comprising:
one or more servers coupled to one or more network interfaces to facilitate access to a network, and memory coupled to the one or more servers and storing instructions that, when executed by the one or more servers, cause the server system to:
transmit, to an end-user computing device via an Internet, a web page configured to indicate an option to receive, from a user, a request via the web page and a browser of the end-user computing device;
process a first indication of a selection of the option;
select an advisor from a plurality of advisors, based at least in part on a compensation rate of the advisor and a quality score of the advisor, for indication in an advertisement for the advisor;
determine a status of the advisor;
in response to the selection, transmit to the end-user computing device the advertisement for the advisor, the advertisement to be visually displayed via the end-user computing device, wherein the advertisement includes:
at least one reference selectable by the user via the Internet to request a real-time communication connection with the advisor, wherein the real-time communication connection is separate from an Internet connection used by the end-user computing device to download the web page; and
an indication of the status of the advisor; and
receive, while the advisor is determined to be currently available for real-time communication, a second indication of a user selection of the at least one reference corresponding to the advisor from the end-user computing device via the advertisement; and
a central controller coupled with the one or more servers and configured to, in response to the second indication of the user selection of the at least one reference, establish a telephonic connection to provide the real-time communication connection requested between the advisor and the user, wherein the establishing the telephonic connection comprises the central controller directing a first transmission to the user, the central controller directing a second transmission to the advisor, and the central controller joining the first transmission and the second transmission, and wherein the telephonic connection is separate from the Internet connection used by the end-user computing device to download the web page.

12. The server system of claim 11, wherein the server system is configured to:
provide visual display of advertisements on a media channel on behalf of multiple advertisers, the visual display of advertisements to include the at least one reference for telephonic connections with respective advertisers of the multiple advertisers; and
charge an amount each time a respective telephonic connection is established between a respective advertiser and a customer.

13. The server system of claim 11, wherein the transmitting the advertisement is in response to a search submitted by the user.

14. The server system of claim 13, wherein the search submitted by the user indicates a geographic location.

15. The server system of claim 13, wherein the search submitted by the user indicates a subject matter.

16. The server system of claim 13, wherein the search submitted by the user comprises a keyword search.

17. The server system of claim 11, wherein the server system is configured to:
charge an amount for each telephonic connection established between the advisor and the user based on the advertisement.

18. The server system of claim 17, wherein the amount charged is according to a price specified by the advisor and the charging of the amount comprises deducting the amount from an amount received from the user and/or charging the user.

19. A method, comprising:
transmitting, by the server system to an end-user computing device via an Internet, a web page configured to indicate an option to receive, from a user, a request via the web page and a browser of the end-user computing device;
processing, by the server system, a first indication of a selection of the option;
selecting, by the server system, an advisor from a plurality of advisors, based at least in part on a compensation rate of the advisor and a quality score of the advisor, for indication in an advertisement for the advisor;
determining, by the server system, a status of the advisor;
in response to the selection, transmitting to the end-user computing device the advertisement for the advisor, the advertisement to be visually displayed via the end-user computing device, wherein the advertisement includes:
at least one reference selectable by the user to request a real-time communication connection with the advisor, wherein the real-time communication connection is separate from an Internet connection used by the end-user computing device to download the web page; and
an indication of the status of the advisor;
while the advisor is determined to be currently available for real-time communication, receiving, by the server system, from the end-user computing device a second indication of a user selection of the at least one reference made via the advertisement, the user selection of the at least one reference corresponding to the advisor; and
in response to the second indication of the user selection of the at least one reference, establishing a telephonic connection via a central controller of the server system to provide the real-time communication connection requested between the advisor and the user, wherein the establishing the telephonic connection comprises the central controller directing a first transmission to the user, the central controller directing a second transmission to the advisor, and the central controller joining the first transmission and the second transmission, and wherein the telephonic connection is separate from the Internet connection used by the end-user computing device to download the web page.

20. The method of claim 19, wherein the transmitting the advertisement is in response to a search submitted by the user.

21. The method of claim 19, further comprising:
providing visual display of advertisements on a media channel on behalf of multiple advertisers, the visual display of advertisements to include the at least one reference for telephonic connections with respective advertisers of the multiple advertisers; and
charging an amount each time a respective telephonic connection is established between a respective advertiser and a customer.

* * * * *